United States Patent
Nöcker et al.

(10) Patent No.: US 12,350,359 B2
(45) Date of Patent: *Jul. 8, 2025

(54) DYEING COMPOSITION COMPRISING DIRECT DYES

(71) Applicant: KAO CORPORATION, Tokyo (JP)

(72) Inventors: Bernd Nöcker, Darmstadt (DE); Qi Uellner, Darmstadt (DE); Fariba Ghiasi, Darmstadt (DE); Steven Breakspear, Darmstadt (DE); Peter Bauer, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/554,694

(22) PCT Filed: Apr. 26, 2022

(86) PCT No.: PCT/EP2022/061031
§ 371 (c)(1),
(2) Date: Oct. 10, 2023

(87) PCT Pub. No.: WO2022/229172
PCT Pub. Date: Nov. 3, 2022

(65) Prior Publication Data
US 2024/0207158 A1 Jun. 27, 2024

(30) Foreign Application Priority Data

Apr. 26, 2021 (EP) .................... 21170395

(51) Int. Cl.
| | | |
|---|---|---|
| *A61Q 5/10* | (2006.01) | |
| *A61K 8/49* | (2006.01) | |
| *A61Q 5/06* | (2006.01) | |

(52) U.S. Cl.
CPC ............ *A61K 8/4953* (2013.01); *A61Q 5/065* (2013.01); *A61K 2800/4322* (2013.01); *A61K 2800/88* (2013.01)

(58) Field of Classification Search
CPC .......... A61K 8/4953; A61K 2800/4322; A61K 2800/88; A61K 8/41; A61K 2800/882; A61K 8/22; A61K 8/19; A61Q 5/065; A61Q 5/10
USPC .......................................................... 8/405
See application file for complete search history.

(56) References Cited

U.S. PATENT DOCUMENTS

| | | | | |
|---|---|---|---|---|
| 4,668,236 | A | * | 5/1987 | Grollier ................. A61K 8/418 8/405 |
| 4,931,066 | A | * | 6/1990 | Grollier ................. A61K 8/418 8/408 |
| 10,052,273 | B2 | * | 8/2018 | Lalleman ............... A61K 8/498 |
| 10,485,744 | B2 | * | 11/2019 | Wahler ...................... A61K 8/41 |
| 2017/0258695 | A1 | * | 9/2017 | Consoli .................. A61K 8/55 |
| 2017/0326048 | A1 | * | 11/2017 | Wahler ..................... A61K 8/19 |

FOREIGN PATENT DOCUMENTS

| | | | | |
|---|---|---|---|---|
| EP | 1813260 | A2 | * 8/2007 | ............... A61Q 5/10 |
| GB | 2 160 900 | A | 1/1986 | |
| WO | WO 2019/057829 | A1 | 3/2019 | |

OTHER PUBLICATIONS

STIC Search Report dated Nov. 12, 2024.*
International Search Report & Written Opinion Issued Aug. 1, 2022, in PCT/EP2022/061031, filed on Apr. 26, 2022, 11 pages.
European Search Report dated Nov. 23, 2021, in EP Application 21170395.4, filed on Apr. 26, 2022, 9 pages.
Database GNPD [Online] Mintel; anonymous: "Phyto Caffeine-Shampoo", Dec. 27, 2017, 4 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A dyeing composition for keratin fibers, containing one or more alkalizing agents, one or more direct dyes, and one or more compounds selected from the following groups:

1)

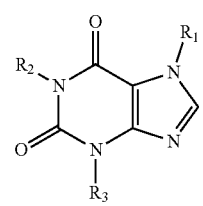

wherein $R_1$, $R_2$, and $R_3$ are independently selected from H and $CH_3$, and 2) one or more imidazolidin-2,4-diones and salts thereof. A total concentration of the one or more alkalizing agents is in a range of 0.5% to 40% by weight, calculated to the total weight of the dyeing composition.

19 Claims, No Drawings

DYEING COMPOSITION COMPRISING DIRECT DYES

CROSS REFERENCE TO RELATED APPLICATIONS

This application is a National Stage entry under 35 U.S.C. § 371 of PCT/EP2022/061031, filed on Apr. 26, 2022, and claims priority to European Patent Application No. 21170395.4, filed on Apr. 26, 2021. The entire contents of both are incorporated herein by reference.

FIELD OF THE INVENTION

The present invention relates to composition for dyeing of keratin fibers with direct dyes. Furthermore, a kit-of-parts and dyeing method is disclosed.

BACKGROUND OF THE INVENTION

Direct dyes have been of particular interest of cosmetic industry over the past decade. In contrast to their oxidative counterparts, direct dyes are easier to apply to keratin fibers, but often lack durability on keratin fibers.

One of the technical challenges with direct dyes in general is their low durability on keratin fibers, which have experienced prior damage due to chemical services such as perming or bleaching. Chemical services alter the internal hair structure and usually allow for improved dye uptake in comparison to virgin hair, but simultaneously direct dyes are also easily washed out. Thus, consumers with prior chemical hair treatments may experience a low durability of the direct dyes, especially after several washes. Moreover, while the color intensity fades over several washes, the hair may experience an additional undesired color shift depending on the different bleeding rates of the individual direct dyes.

In everyday business operation of a hair dresser salon it is also not always easy for the professional to analyze prior hair damage of the customer, as some prior treatments may have already washed out and their effect is not visible anymore. While assuming healthy hair and then performing direct dyeing, it may come to a surprise to the hair dresser as well as the customer that durability of the dyeing treatment is exceptionally low. Such experiences will certainly frustrate every party.

In summary, the prior art has not satisfactorily solved the above challenges, and, therefore, there is a real need to develop direct dyeing compositions for keratin fibers, which deliver high dyeing intensity and have good durability, regardless of the history of chemical treatments.

SUMMARY OF THE INVENTION

The first object of the present invention is a dyeing composition A for keratin fibers, preferably for human keratin fibers, more preferably for human hair, comprising:
a) one or more alkalizing agent(s),
b) one or more direct dye(s),
c) one or more compound(s) selected from the following groups:

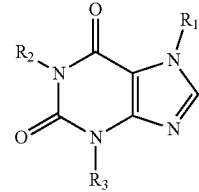

1)

wherein $R_1$, $R_2$, and $R_3$ are independently selected from H and $CH_3$, and/or their mixtures,
2) one or more imidazolidin-2,4-dione(s) and/or their derivatives, and/or their mixtures, and/or their salt(s),
wherein one or more direct dye(s) as compound(s) according to group b) is/are selected from Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, Acid Red 52, DC Violet 2, DC Red 33, DC Orange 4, DC Red 27, DC Yellow 10, HC Blue 18, HC Red 18, HC Yellow 16, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87, Basic Orange 31, HC Blue 17 and Basic Blue 124, HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-amino-6-chloro-4-nitrophenol, and/or their mixtures, and/or their salt(s), and
wherein the total concentration of alkalizing agent(s) as compound(s) according to group a), preferably the total concentration of one or more alkanolamine(s) and/or its/their salt(s) and/or ammonia and/or its salt(s), is in the range of 0.5% to 40% by weight, calculated to the total weight of composition A.

The second object of the present invention is a hair dyeing composition as defined above having a pH in the range of 7 to 12, preferably in the range of 8 to 11.5, more preferably in the range of 9 to 11, and optionally comprising one or more oxidizing agent(s), preferably hydrogen peroxide.

The third object of the present invention is a kit-of-parts for dyeing keratin fibers, preferably human keratin fibers, more preferably human hair, comprising:
a composition A as defined above,
a composition B having a pH in the range of 1 to 6 and optionally comprising one or more oxidizing agent(s).

The fourth object of the present invention is a kit-of-parts for dyeing keratin fibers, preferably human keratin fibers, more preferably human hair, comprising:
a first composition comprising one or more compound(s) according to group b) as defined above,
a second composition comprising one or more compound(s) according to group c) as defined above,
wherein the first and/or second and/or an optional third composition comprises one or more compound(s) according to group a) as defined above.

The fifth object of the present invention is a method for dyeing of keratin fibers, preferably human keratin fibers, more preferably human hair, comprising the steps of:
i) providing a composition A as defined in the claims 1 to 12, optionally a composition B as defined in claim 13, and/or optionally one or more further composition(s),
ii) optionally mixing the compositions A and B, or the compositions A and one further composition(s), or the compositions A, B, and one or more further composition(s), to yield a ready-to-use composition having a pH in the range of 7 to 12,
iii) applying the composition A or the ready-to-use composition of step ii) onto keratin fibers,
iv) leaving the composition A or the ready-to-use composition for a time period of 1 to 60 min and optionally heating the keratin fibers to a temperature range in the range of 40° C. to 60° C.,
v) rinsing off the keratin fibers and optionally shampooing the keratin fibers.

The sixth object of the present invention is a method of making composition A as defined above comprising the steps of:
providing a first composition comprising one or more compound(s) according to group b) as defined above,
providing a second composition comprising one or more compound(s) according to group c) as defined above,
with the provision that the first and/or second and/or an optional third composition comprise(s) one or more compound(s) according to group a) as defined above,
mixing the first, second, and optionally third composition.

DETAILED DESCRIPTION OF THE INVENTION

Inventors of the present invention have unexpectedly found out that a composition according to claim 1 has increased dyeing intensity and showed increased durability of direct dyes. Furthermore, the cosmetic appearance of keratin fibers was improved. The latter effects are related to shine and healthy feel.

Composition A

The present invention is directed to a dyeing composition A for keratin fibers, preferably for human keratin fibers, more preferably for human hair, comprising:
a) one or more alkalizing agent(s),
b) one or more direct dye(s),
c) one or more compound(s) selected from the following groups:

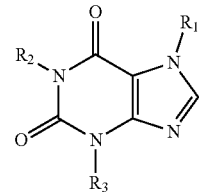

wherein $R_1$, $R_2$, and $R_3$ are independently selected from H and $CH_3$, and/or their mixtures, 2) one or more imidazolidin-2,4-dione(s) and/or their derivatives, and/or their mixtures, and/or their salt(s), wherein one or more direct dye(s) as compound(s) according to group b) is/are selected from Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, Acid Red 52, DC Violet 2, DC Red 33, DC Orange 4, DC Red 27, DC Yellow 10, HC Blue 18, HC Red 18, HC Yellow 16, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87, Basic Orange 31, HC Blue 17 and Basic Blue 124, HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-amino-6-chloro-4-nitrophenol, and/or their mixtures, and/or their salt(s), and wherein the total concentration of alkalizing agent(s) as compound(s) according to group a), preferably the total concentration of one or more alkanolamine(s) and/or its/their salt(s) and/or ammonia and/or its salt(s), is in the range of 0.5% to 40% by weight, calculated to the total weight of composition A.

Compound(s) According to Group a)

The composition A of the present invention comprises one or more alkalizing agent(s) as compound(s) according to group a).

It is preferred from the viewpoint of providing alkalinity and cosmetic safety that one or more alkalizing agent(s) is/are one or more organic alkalizing agent(s) and/or ammonia and/or its salt(s).

Preferably, one or more organic alkalizing agent(s) are selected from alkyl and/or alkanolamine(s) and/or its/their salt(s), more preferably they/it is selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethane and/or its/their salt(s), and/or their mixtures, from the viewpoint of providing alkalinity and cosmetic safety as well as their low odor.

The total concentration of alkalizing agent(s) as compound(s) according to group a) in the composition of the present invention, preferably the total concentration of one or more alkanolamine(s) and/or its/their salt(s) and/or ammonia and/or its salt(s), is in the range of 0.5% to 40% by weight, calculated to the total weight of composition A.

The most preferred alkalizing agent(s) as compound(s) according to group a) is/are selected from monoethanolamine, 2-amino-2-methylpropanol, tris-(hydroxymethyl)-aminomethane, and/or its/their salt(s), ammonia and or its salt(s), and/or their mixtures, from the viewpoint of providing alkalinity and cosmetic safety.

In one aspect of the present invention, it may be suitable from the viewpoint of storage stability that one or more alkalizing agent(s) is one or more inorganic alkalizing agent(s), preferably selected from metasilicates, carbonates, and/or bicarbonates, and/or their alkali or earth alkali salts, and/or their mixtures, preferably it is sodium metasilicate.

It is preferred from the viewpoint of providing alkalinity that the total concentration of alkalizing agent(s), preferably the total concentration of one or more alkanolamine(s) and/or its/their salt(s) and/or ammonia and/or its salt(s), is 0.75% by weight or more, more preferably 1% by weight or more, calculated to the total weight of the composition A.

It is preferred from the viewpoint of providing alkalinity, hair damage, and odor that the total concentration of alkalizing agent(s), preferably the total concentration of one or more alkanolamine(s) and/or its/their salt(s) and/or ammonia and/or its salt(s), is 40% by weight or less, more preferably 30% by weight or less, further more preferably 25% by weight or less, calculated to the total weight of the composition A.

For attaining the above-mentioned effects, it is preferred that the total concentration of alkalizing agent(s), preferably the total concentration of one or more alkanolamine(s) and/or its/their salt(s) and/or ammonia and/or its salt(s), is in the range of 0.5% to 30% by weight, preferably in the range of 0.5% to 25% by weight, more preferably in the range of 0.75% to 25% by weight, still more preferably in the range of 1% to 25% by weight, calculated to the total weight of the composition A.

Compound(s) According to Group b)

The composition A of the present invention comprises one or more direct dye(s) as compound(s) according to group b).

In principle, all direct dyes are suitable for the purpose of the present inventions. In particular, anionic, cationic, or neutral direct dyes are suitable.

Preferably, one or more direct dye(s) according to group b) is/are selected from Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, Acid Red 52, DC Violet 2, DC Red 33, DC Orange 4, DC Red 27, DC Yellow 10, HC Blue 18, HC Red 18, HC Yellow 16, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87, Basic Orange 31, HC Blue 17 and Basic Blue 124, HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, and/or their mixtures, and/or their salt(s), from the viewpoint of color intensity.

It is further preferred from the viewpoint of dyeing intensity and wash fastness, that one or more direct dye(s) is selected from HC Blue 18, HC Red 18, HC Yellow 16, Disperse Black 9, Acid Yellow 1, and/or their salt(s), and/or their mixtures.

The most preferred direct dyes as compound(s) according to group b) is/are HC Blue 18, HC Red 18, HC Yellow 16, and/or their salt(s), and/or their mixtures.

It is preferred from the viewpoint of color intensity that the total concentration of compound(s) according to group b) is 0.001% by weight or more, further preferably 0.005% by weight or more, still more preferably 0.01% by weight or more, calculated to the total weight of the composition A.

It is preferred from the viewpoint of color intensity and economic reasons that the total concentration of compound(s) according to group b) is 10% by weight or less, further preferably 5% by weight or less, still more preferably 3% by weight or less, still further more preferably 2% by weight or less, still further more preferably 1.5% by weight or less, calculated to the total weight of the composition A.

For attaining the above-mentioned effects, it is preferred that the total concentration of compound(s) according to group b) is in the range of 0.001% to 10% by weight, preferably in the range of 0.005% to 5% by weight, more preferably in the range of 0.01% to 3% by weight, still further more preferably in the range of 0.01% to 2% by weight, still further more preferably in the range of 0.01% to 1.5% by weight, calculated to the total weight of the composition A.

Compound(s) According to Group c)

The composition A of the present invention comprises one or more compound(s) according to group c) selected from the following groups:

1)

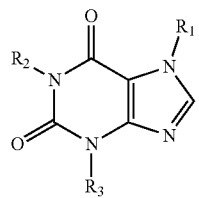

wherein $R_1$, $R_2$, and $R_3$ are independently selected from H and $CH_3$, and/or their mixtures, 2) one or more imidazolidin-2,4-dione(s) and/or their derivatives, and/or their mixtures, and/or their salt(s).

The compound(s) according to group c1) is/are xanthine(s) and its/their derivatives.

Suitable xanthine and/or xanthine derivatives according to the structure of compound c1) are Xanthine with $R_1=R_2=R_3=H$,
Theobromine with $R_1=R_3=CH_3$ and $R_2=H$,
Theophylline with $R_2=R_3=CH_3$ and $R_1=H$, and
Caffeine with $R_1=R_2=R_3=CH_3$.

Mixtures of the above are suitable as well.

It is preferred from economic viewpoint that at least one or more compound(s) according to group c1) is/are caffeine and/or theobromine, and/or their mixtures, preferably it is caffeine.

Thus, the disclosure of the present invention is also directed to a dyeing composition A for keratin fibers, preferably for human keratin fibers, more preferably for human hair, comprising:
a) one or more alkalizing agent(s),
b) one or more direct dye(s),
c) one or more compound(s) selected from the following groups:

1)

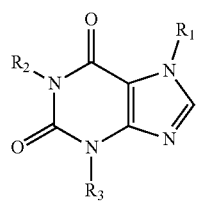

wherein $R_1$, $R_2$, and $R_3$ are independently selected from H and $CH_3$, and/or their mixtures.

It is preferred from the viewpoint of commercial availability that one or more compound(s) according to group c2) is according to the following general structure:

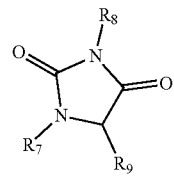

wherein $R_7$, $R_8$, and $R_9$ are independently selected from H, OH, halogen, $C_1$-$C_{12}$ linear or branched alkyl or alkenyl, O—X, COOH, phenyl, diphenyl, ureyl, and/or their salt(s), and/or their mixtures, with X being $C_1$-$C_{12}$ linear or branched alkyl.

It is preferred from the viewpoint of commercial availability that one or more compound(s) according to group c2) is/are
hydantoin,
dichlordimethylhydantoin,
bromchlordimethylhydantoin,
dibromdimethylhydantoin,
ethotoin,
phenytoin,
mephenytoin,
fosphenytoin,
allantoin,
and/or their salt(s), and/or their mixtures.

It is preferred from the viewpoint of commercial availability and dyeing intensity that one or more compound(s) according to group c2) is hydantoin or allantoin, and/or their salt(s), and/or their mixtures, preferably it is hydantoin and/or its salt(s).

Thus, the disclosure of the present invention is also directed to a dyeing composition A for keratin fibers, preferably for human keratin fibers, more preferably for human hair, comprising:
a) one or more alkalizing agent(s),
b) one or more direct dye(s),
c) one or more compound(s) selected from the following groups:
2) one or more imidazolidin-2,4-dione(s) and/or their derivatives, and/or their mixtures, and/or their salt(s).

It is further preferred from the viewpoint of stabilizing performance that the total concentration of compounds according to group c) is 0.001% by weight or more, more preferably 0.005% by weight or more, further more preferably 0.01% by weight or more, still more preferably 0.025% by weight or more, calculated to the total weight of the composition A.

It is further preferred from the viewpoint of economic reasons as well as stabilizing performance that the total concentration of compounds according to group c) is 0.5% by weight or less, more preferably 0.25% by weight or less, further more preferably 0.2% by weight or less, still more preferably 0.15% by weight or less, calculated to the total weight of the composition A.

For attaining the above-mentioned effects, it is preferred that It is preferred from the viewpoint of stabilization and dyeing intensity that that the total concentration of compounds according to group c) is in the range of 0.001% to 0.5% by weight, preferably in the range of 0.005% to 0.25% by weight, more preferably in the range of 0.01% to 0.2% by weight, still more preferably in the range of 0.025% to 0.15% by weight, calculated to the total weight of the composition A.

It is preferred from the viewpoint of dyeing performance that the weight ratio of compounds groups b) to c) in the composition A is 2 or more, more preferably 20 or more, further more preferably 37.5 or more, further more preferably 100 or more.

It is preferred from the viewpoint of dyeing performance that the weight ratio of compounds groups b) to c) in the composition A is 1,000 or less, more preferably 600 or less, further more preferably 400 or less, further more preferably 150 or less.

For achieving the above-mentioned effects, it is preferred that the weight ratio of compounds groups b) to c) in the composition A is in the range of 2 to 1,000, more preferably in the range of 20 to 600, further more preferably in the range of 37.5 to 400, further more preferably in the range of 100 to 150.

Forms of Composition A

The first composition A of the present invention may be available in various cosmetic forms such as aqueous composition or powder composition.

Powder Composition

In one aspect of the present invention, the composition A may be a powder composition.

The term 'powder' denotes a solid composition at 25° C. and atmospheric pressure. The term relates to freely flowing powders as well as compressed powders such as tablets. The powder composition may also comprise water as long as its nature of the solid state at 25° C. is unchanged. Depending on the type of powder, a water content of 10% by weight or less, calculated to the total weight of composition A, may be acceptable. This does not exclude the presence of residual moisture from air or crystal water bound to ingredients. Preferably, composition A is an anhydrous powder composition, from the viewpoint of stability.

It is preferred from the viewpoint of composition stability and convenience of use that composition A comprises one or more pulverulent excipient.

The term 'excipient' denotes a compound, which may act as filling material and dispersant for the other compounds of composition A and do not react with the dyes and the alkalizing agent and, thus, confer the powder a high degree of storage stability over an extended period of time.

Composition A of the present invention may comprise an organic and/or an inorganic pulverulent excipient in which the alkalizing agent and direct dyes are dispersed.

Suitable organic and/or an inorganic pulverulent excipients are, for example, diatomaceous earth, kaolin, bentonite, starch especially corn, tapioca, rice, wheat and potato, nylon powder, montmorillonit, gypsum, sawdust and perlite.

The total concentration of organic and/or an inorganic pulverulent excipient preferably is 50% by weight or more, more preferably 55% by weight or more, further more preferably 60% by weight or more, still further more preferably 65% by weight or more, even further more preferably 70% by weight or more, even more preferably 75% by weight or more, calculated to the total weight of composition A, from the viewpoint of achieving good dispersability of the direct dyes in the powder and quick dissolution of the powder.

The total concentration of organic and/or an inorganic pulverulent excipient preferably is 98% by weight or less, more preferably 95% by weight or less, further more preferably 90% by weight or less, calculated to the total weight of composition A, from the viewpoint of achieving good dispersability of the direct dyes in the powder and formulation freedom.

For attaining the above mentioned effects, the total concentration of organic and/or an inorganic pulverulent excipient preferably is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total weight of composition A.

Liquid Composition Comprising Less than 1% by Weight of Water

In another aspect of the present invention, composition A is a liquid composition at 25° C. and atmospheric pressure comprising one or more organic solvent(s) as compound(s) and less than 1% by weight of water, calculated to the total weight of composition A. Preferably, the composition is anhydrous, from the viewpoint of dye stability.

The term 'liquid' denotes a physical state at 25° C. and atmospheric pressure, i.e., the dyeing composition is liquid at room temperature.

The term 'anhydrous' denotes a composition, which is free of added water. This does not exclude the presence of residual moisture from air or crystal water bound to ingredients.

For this aspect of the present invention, composition A may comprise one or more organic solvent(s).

The organic solvent(s) may be selected to dissolve the alkalizing agents and dyes. Preferred solvents are mono-, di-, and trivalent alcohols and/or their mixtures.

Preferred mono-, di-, and trivalent alcohols from the viewpoint of cosmetic safety and dissolution capacity are ethanol, n-propanol, isopropanol, propylene glycol, ethylene glycol, benzyl alcohol, phenoxyethanol, and glycerol, and/or their mixtures.

It is further preferred from the viewpoint of solution stability that the total concentration of organic solvents is 75% by weight or more, more preferably 80% by weight or more, further more preferably 85% by weight or more, calculated to the total weight of composition A.

It is further preferred from the viewpoint of dyeing intensity that the total concentration of organic solvents is 98% by weight or less, more preferably 95% by weight or less, further more preferably 92% by weight or less, calculated to the total weight of composition A.

For attaining the above-mentioned effects, it is preferred that the total concentration of organic solvents is in the range of 75% to 98% by weight, more preferably 80% to 95% by weight, further more preferably in the range of 85% to 92% by weight, calculated to the total weight of composition A.

Aqueous Composition

In one aspect of the present invention, composition A is an aqueous composition.

The term 'aqueous' denotes a composition that comprises a majority of water, i.e., composition A preferably comprises water at 50% by weight or more, further more preferably at 60% by weight or more, still more preferably at 70% by weight or more, still further more preferably at 80% by weight or more, calculated to the total weight of composition A, from the viewpoint of achieving a cosmetically acceptable composition.

It is further preferred from the viewpoint of dyeing intensity that composition A comprises water at 98% by weight or less, more preferably at 95% by weight or less, further more preferably at 92% by weight or less, calculated to the total weight of composition A.

For achieving the above-mentioned effects, it is preferred that the total concentration of water in composition A is in the range of 50% to 98% by weight, more preferably in the range of 60% to 95% by weight, further more preferably in the range of 70% to 92% by weight, still more preferably in the range of 80% to 92% by weight, calculated to the total weight of composition A.

It is preferred from the viewpoint of dyeing performance that the pH of composition A is 7 or more, more preferably the pH is 7.5 or more, further more preferably the pH is 8 or more, still further more preferably the pH is 9 or more.

It is preferred from the viewpoint of hair damage and dyeing performance that the pH of composition A is 12 or less, more preferably the pH is 11 or less, still more preferably the pH is 10.5 or less.

For attaining the above mentioned effects, it is preferred that the pH of composition A is in the range of 7 to 12, preferably in the range of 8 to 11.5, further more preferably in the range of 9 to 11.5, further more preferably in the range of 9 to 10.5.

It is further preferred that the aqueous or powder composition A comprises one or more organic solvent(s), as explained for the aspect having less than 1% by weight of water.

Preferred organic solvents in such a case are ethanol, benzyl alcohol, and/or phenoxyethanol, and/or their mixtures, from the viewpoint of enhancing color intensity.

Preferred concentrations of organic solvents are in the range of 1% to 15% by weight, preferably in the range of 2% to 10% by weight, more preferably in the range of 2% to 8% by weight, calculated to the total weight of composition A, from the viewpoint of enhancing color intensity.

Lipophilic Compounds as Compounds According to d)

The composition A of the present invention may comprises one or more lipophilic compound(s) as compound(s) according to group d).

Preferably, compounds according to group d) are selected from $C_{12}$ to $C_{22}$ fatty alcohols, esters of $C_3$ to $C_{22}$ alcohols with $C_{12}$ to $C_{22}$ fatty acids, $C_8$ to $C_{22}$ fatty acids, vegetable oils, and/or silicones, and/or hydrocarbon-based products, and/or their mixtures, from the viewpoint of cosmetic compatibility.

Suitable $C_{12}$ to $C_{22}$ fatty alcohols are myristyl alcohol, cetyl alcohol, stearyl alcohol, behenyl alcohol, and cetearyl alcohol.

Suitable esters of $C_3$ to $C_{22}$ alcohols with $C_{12}$ to $C_{22}$ fatty acids are isopropyl myristate, isopropyl palmitate, and myristyl myristate.

Suitable $C_8$ to $C_{22}$ fatty acids are oleic acid, linoleic acid, and palmitic acid.

Suitable vegetable oils are olive oil, almond oil, sunflower oil, and argan oil.

Suitable silicones are non-aminated and/or aminated silicones. The latter are commonly known as amodimethicones.

It is preferred from the viewpoint of forming a stable composition and user friendliness that the total concentration of compounds according to group d) is 1% by weight or more, more preferably 2% by weight or more, further more preferably 3% by weight or more, calculated to the total weight of composition A.

It is preferred from the viewpoint of forming a stable composition that the total concentration of compounds according to group d) is 20% by weight or less, more preferably 15% by weight or less, further more preferably 12% by weight or less, calculated to the total weight of composition A.

For attaining the above-mentioned effects, the total concentration of compounds according to group d) is in the range of 1% to 20% by weight, preferably in the range of 2% to 15% by weight, more preferably in the range of 3% to 12% by weight, calculated to the total weight of composition A.

Surfactants as Compounds According to e)

The composition A of the present invention may further comprise one or more surfactant(s) as compound according to group e), preferably selected from non-ionic surfactants, anionic surfactants, cationic surfactants, and/or amphoteric/zwitterionic surfactants, and/or their salt(s), and/or their mixtures, more preferably selected from anionic surfactants and/or their salt(s), from the viewpoint of stabilizing the composition and improving wettability and mixability.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures, and/or their salts.

Suitable examples are alkyl sulfate or preferably ethoxylated alkyl ether sulfate surfactants or mixtures thereof, and/or salts thereof, having an alkyl chain length of $C_{10}$ to $C_{22}$ and an ethoxylation degree from 1 to 50.

Suitable non-ionic surfactants may be selected from alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants, and/or their salts. Suitable examples are cetrimonium chloride and behentrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

Suitable concentration ranges for surfactants are in the range of 0.1% to 10% by weight, calculated to the total weight of composition A, from the viewpoint of enhancing wettability of keratin fibers, physical stability, and mixability with other compositions.

Thickening Polymers

From the viewpoint of cosmetic safety, it is further preferred that the composition A of the present invention comprises one or more thickening polymer.

The composition A of the present invention comprises one or more thickening polymer(s) selected from non-ionic thickening polymers and/or anionic thickening polymers, and/or their mixtures.

Preferably, the thickening polymers are selected from polymers resulting in an aqueous solution and/or aqueous dispersion at pH between 1 and 6 having a viscosity of at least 1,000 mPa·s measured at a polymer concentration of 1% by weight in water at 25° C. determined by cone plate viscometry at 25° C. under atmospheric conditions, calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as ($C_2$-$C_8$)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

Suitable synthetic anionic polymers are associative thickening polymers, such as acrylates/steareth-30 methacrylate copolymer.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers of the present invention are 0.1% by weight or more, more preferably 0.25% by weight or more, more preferably 0.5% by weight or more, calculated to the total weight of the composition, from the viewpoint of providing sufficient viscosity to the composition A.

Preferably, the total concentration of thickening polymers of the present invention are 15% by weight or less, more preferably 12% by weight or more, further more preferably 10% by weight or less, calculated to the total weight of composition A, from the viewpoint of providing sufficient viscosity to the composition and cost of goods.

For attaining the above-mentioned effects, it is preferred that the total concentration of thickening polymers in composition A of the present invention is in the range of 0.1% to 15% by weight, preferably in the range of 0.25% to 12% by weight, more preferably in the range of 0.5% to 10% by weight, calculated to the total weight of composition A.

It is preferred from the viewpoint of cosmetic safety that the compositions A and/or B, in case that they are liquid, have a viscosity in the range of 1,000 Pas to 25,000 mPas, preferably 2,000 mPas to 20,000 mPas, more preferably in the range of 2,500 mPas to 17,500 mPas, determined by cone plate viscometry at 25° C. under atmospheric conditions. A suitable viscometer is a Brookfield viscometer with spindle #4.

Optionally, composition A as defined above has a pH in the range of 7 to 12, preferably in the range of 8 to 11.5, more preferably in the range of 9 to 11, and comprises one or more oxidizing agent(s), preferably hydrogen peroxide.

It is further preferred from the viewpoint of dyeing performance that the concentration of hydrogen peroxide in composition A is 0.1% by weight or more, more preferably 0.25% by weight or more, further more preferably 1% by weight or more, calculated to the total weight of composition A.

It is further preferred from the viewpoint of product performance and user safety that the concentration of hydrogen peroxide in composition A is 20% by weight or less, more preferably 15% by weight or less, further more preferably 12% by weight or less, calculated to the total weight of composition A.

For attaining the above-mentioned effects, it is preferred that the concentration of hydrogen peroxide in the composition A is in the range of 0.1% to 20% by weight, more preferably in the range of 0.25% to 15% by weight, further more preferably in the range of 1% to 12% by weight, calculated to the total weight of composition A.

Kit-of-Parts

The present invention is also directed to a kit-of-parts for dyeing keratin fibers, preferably human keratin fibers, more preferably human hair, comprising:

a composition A as defined above, and a composition B having a pH in the range of 1 to 6 and optionally comprising one or more oxidizing agent(s).

Composition B preferably is a liquid composition from the viewpoint of user convenience. Preferably, from the viewpoint of stability, composition B has a pH in the range of 1.5 to 5, further more preferably in the range of 2 to 4.5

Composition B preferably is an emulsion, thickened gel, or a combination thereof, from the viewpoint of cosmetic safety as well as user friendliness. It may comprise lipophilic compound(s) according to group d) and/or surfactant(s) according to group e) and/or one or more thickening polymer(s) as defined above.

Composition B may further comprise one or more oxidizing agent(s). The preferred oxidizing agent is hydrogen peroxide.

Suitable concentration ranges for hydrogen peroxide in composition B is/are in the range of 0.1% to 20% by weight, more preferably in the range of 0.25% to 15% by weight, further more preferably in the range of 1% to 12% by weight, calculated to the total weight of composition B.

Composition B of the present invention may comprise one or more lipophilic compound(s) as compound(s) according to group d), as defined for composition A above.

It is preferred from the viewpoint of forming a stable composition and user friendliness that the total concentration of compounds according to group d) is 1% by weight or more, more preferably 2% by weight or more, further more preferably 3% by weight or more, calculated to the total weight of composition B.

It is preferred from the viewpoint of forming a stable composition that the total concentration of compounds according to group d) is 20% by weight or less, more preferably 15% by weight or less, further more preferably 12% by weight or less, calculated to the total weight composition B.

For attaining the above-mentioned effects, the total concentration of compounds according to group d) is in the range of 1% to 20% by weight, preferably in the range of 2% to 15% by weight, more preferably in the range of 3% to 12% by weight, calculated to the total weight of composition B.

Composition B of the present invention may further comprise one or more surfactant(s) as compound according to group e), as defined above for composition A.

Suitable concentration ranges for surfactants are in the range of 0.1% to 10% by weight, calculated to the total weight of composition B, from the viewpoint of enhancing wettability of keratin fibers, physical stability, and mixability with other compositions.

From the viewpoint of cosmetic safety, it is further preferred that the composition B of the present invention comprises one or more thickening polymer, as defined for composition A above.

Preferably, the total concentration of thickening polymers of the present invention are 0.1% by weight or more, more preferably 0.25% by weight or more, more preferably 0.5% by weight or more, calculated to the total weight of composition B, from the viewpoint of providing sufficient viscosity to the composition B.

Preferably, the total concentration of thickening polymers of the present invention are 15% by weight or less, more preferably 12% by weight or more, further more preferably 10% by weight or less, calculated to the total weight of composition B, from the viewpoint of providing sufficient viscosity to the composition and cost of goods.

For attaining the above-mentioned effects, it is preferred that the total concentration of thickening polymers in composition B of the present invention is in the range of 0.1% to 15% by weight, preferably in the range of 0.25% to 12% by weight, more preferably in the range of 0.5% to 10% by weight, calculated to the total weight of composition B.

It is preferred from the viewpoint of cosmetic safety that B has a viscosity in the range of 1,000 Pas to 25,000 mPas, preferably 2,000 mPas to 20,000 mPas, more preferably in the range of 2,500 mPas to 17,500 mPas, determined by cone plate viscometry at 25° C. under atmospheric conditions. A suitable viscometer is a Brookfield viscometer with spindle #4.

Optionally, the kit-of-parts further comprises one or more compositions selected from:
- a bleaching powder composition C comprising one or more persalt(s) and/or peroxy salt(s) and one or more alkalizing agent(s),
- an aqueous lightening composition D comprising one or more alkalizing agent(s) and having a pH in the range of 7 to 12.

The present invention is also directed to a kit-of-parts for dyeing keratin fibers, preferably human keratin fibers, more preferably human hair, comprising:
- a first composition comprising one or more compound(s) according to group b) as defined above,
- a second composition comprising one or more compound(s) according to group c) as defined above,
- wherein the first and/or second and/or an optional third composition comprises one or more compound(s) according to group a) as defined above.

The compositions of the kit are kept separate until directly prior to use onto keratin fibers. Then the compositions are mixed to prepare composition A as defined above.

Bleaching Powder Composition C

It is further preferred that the bleaching powder composition C comprises one or more persalt(s) and/or peroxy salt(s) as bleaching compound(s) and one or more alkalizing agent(s).

Bleaching powder composition C comprises one or more persalt(s) and/or peroxy salt(s). Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid.

The preferred persalts from the viewpoint of bleaching power are sodium, potassium and ammonium persulfate.

It is preferred from the viewpoint of bleaching power and cosmetic safety that the total concentration of persalts and/or peroxy salts in the bleaching powder composition C is in the range of 10% to 80% by weight, preferably in the range of 15% to 70% by weight, more preferably in the range of 20% to 60% by weight, and still more preferably in the range of 25% to 60% by weight, calculated to the total weight of bleaching powder composition C.

Bleaching powder composition C further comprises one or more alkalizing agent(s). Suitable alkalizing agent(s) are metasilicates and disilicates, in particular sodium metasilicate and/or sodium disilicate. It is preferred from the viewpoint of alkalinity that the concentration of metasilicates and/or disilicates, and/or their salts, in bleaching powder composition C is in the range of 1% to 20% by weight, more preferably 5% to 15% by weight, calculated to the total weight of bleaching powder composition C.

Other suitable alkalizing agent(s) are carbonate and bicarbonate alkali salts such as sodium, potassium, and ammonium salts. The preferred salts are bicarbonate salts and especially preferred is ammonium bicarbonate, from the viewpoint of buffer capacity. Suitable concentration of carbonates in the bleach powder composition is in the range of 0.25% to 10% by weight, preferably in the range of 0.5% to 7.5% by weight, more preferably in the range of 0.75% to 5% by weight, and still more preferably in the range of 1% to 4% by weight, calculated to the total weight of bleaching powder composition C, from the viewpoint of buffer capacity and low hair damage.

Aqueous Lightening Composition D

Preferably, the aqueous lightening composition D is an emulsion comprising one or more lipophilic compound according to d), as also disclosed for composition A, from the viewpoint of user convenience.

Aqueous lightening composition D preferably has a pH in the range of 8 to 11, more preferably in the range of 8.5 to 10.5, from the viewpoint of lightening performance. Suitable alkalizing agents are disclosed above for composition A.

Method for Dyeing

The present invention is also directed to a method for dyeing of keratin fibers, preferably human keratin fibers, more preferably human hair, comprising the steps of:
i) providing a composition A as defined in the claims 1 to 12, optionally a composition B as defined in claim 13, and/or optionally one or more further composition(s),
ii) optionally mixing the compositions A and B, the compositions A and one further composition(s), or the compositions A, B, and one or more further composition(s), to yield a ready-to-use composition having a pH in the range of 7 to 12,
iii) applying the composition A or the ready-to-use composition of step ii) onto keratin fibers,
iv) leaving the composition A or the ready-to-use composition for a time period of 1 to 60 min and optionally heating the keratin fibers to a temperature range in the range of 40° C. to 60° C.,
v) rinsing off the keratin fibers and optionally shampooing the keratin fibers.

The ready-to-use composition is then applied to keratin fibers and left for a time period of 1 min to 60 min as defined in step iv). Preferred time ranges for step iv) are 5 min to 45 min, more preferred ranges are 10 min to 35 min, from the viewpoint of sufficiently dyeing.

Optionally, heat may be applied while leaving the composition A or the ready-to-use composition onto keratin fibers. Suitable temperature ranges are 30° C. to 50° C.

It is preferred from the viewpoint of bleaching power that one or more further composition(s) in steps ii) and iii) are the bleaching powder composition C and/or the aqueous lightening composition D as defined above.

The present invention is also directed to <1> a dyeing composition A for keratin fibers, preferably for human keratin fibers, more preferably for human hair, comprising:
a) one or more alkalizing agent(s),
b) one or more direct dye(s),
c) one or more compound(s) selected from the following groups:

1)

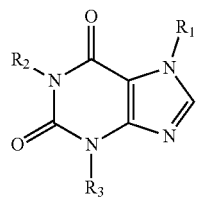

wherein $R_1$, $R_2$, and $R_3$ are independently selected from H and $CH_3$, and/or their mixtures, 2) one or more imidazolidin-2,4-dione(s) and/or their derivatives, and/or their mixtures, and/or their salt(s), wherein one or more direct dye(s) as compound(s) according to group b) is/are selected from Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, Acid Red 52, DC Violet 2, DC Red 33, DC Orange 4, DC Red 27, DC Yellow 10, HC Blue 18, HC Red 18, HC Yellow 16, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87, Basic Orange 31, HC Blue 17 and Basic Blue 124, HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-amino-6-chloro-4-nitrophenol, and/or their mixtures, and/or their salt(s), and
wherein the total concentration of alkalizing agent(s) as compound(s) according to group a), preferably the total concentration of one or more alkanolamine(s) and/or its/their salt(s) and/or ammonia and/or its salt(s), is in the range of 0.5% to 40% by weight, calculated to the total weight of composition A.

<2> The composition according to clause <1> characterized in that one or more alkalizing agent(s) as compound(s) according to group a) is/are one or more organic alkalizing agent(s) and/or ammonia and/or its salt(s).

<3> The composition according to any of the clauses <1> to <2> characterized in that one or more compound(s) according to a) is/are one or more organic alkalizing agent(s) and/or ammonia and/or its salt(s), preferably it is one or more alkanolamine(s) and/or its/their salt(s) and/or ammonia and/or its salt(s), more preferably it is selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethan and/or its/their salt(s), and/or their mixtures, most preferably it is selected from monoethanolamine, 2-amino-2-methylpropanol, tris-(hydroxymethyl)-aminomethan, ammonia and or its/their salt(s), and/or their mixtures.

<4> The composition according to any of the clauses <1> to <3> characterized in that one or more alkalizing agent(s) as compound(s) according to a) is one or more inorganic alkalizing agent(s), preferably selected from metasilicates, carbonates, and/or bicarbonates, and/or their alkali or earth alkali salts, and/or their mixtures, preferably it is sodium metasilicate.

<5> The composition according to any of the clauses <1> to <4> characterized in that the total concentration of alkalizing agent(s) as compound(s) according to group a), preferably the total concentration of one or more alkanolamine(s) and/or its/their salt(s) and/or ammonia and/or its salt(s), is in the range of 0.5% to 30% by weight, preferably in the range of 0.5% to 25% by weight, more preferably in the range of 0.75% to 25% by weight, still more preferably in the range of 1% to 25% by weight, calculated to the total weight of composition A.

<6> The composition according to any of the clauses <1> to <5> characterized in that one or more direct dye(s) as compound(s) according to group b) is/are selected from HC Blue 18, HC Red 18, HC Yellow 16, Disperse Black 9, Acid Yellow 1, 2-amino-6-chloro-4-nitrophenol, and/or their salt(s), and/or their mixtures.

<7> The composition according to any of the clauses <1> to <6> characterized in that one or more direct dye(s) as compound(s) according to group b) is/are selected from HC Blue 18, HC Red 18, HC Yellow 16, and/or their salt(s), and/or their mixtures.

<8> The composition according to any of the clauses <1> to <7> characterized in that the total concentration of compound(s) according to group b) is in the range of 0.001% to 10% by weight, preferably in the range of 0.005% to 5% by weight, more preferably in the range of 0.01% to 3% by weight, still further more preferably in the range of 0.01% to 2% by weight, still further more preferably in the range of 0.01% to 1.5% by weight, calculated to the total weight of composition A.

<9> The composition according to any of the clauses <1> to <8> characterized in that one or more compound(s) according to group c1) is/are
Xanthine with $R_1=R_2=R_3=H$,
Theobromine with $R_1=R_3=CH_3$ and $R_2=H$,
Theophylline with $R_2=R_3=CH_3$ and $R_1=H$, and
Caffeine with $R_1=R_2=R_3=CH_3$, and/or their mixtures.

<10> The composition according to any of the clauses <1> to <9> characterized in that one or more compound(s) according to group c1) is/are caffeine and/or theobromine, and/or their mixtures, preferably it is caffeine.

<11> The composition according to any of the clauses <1> to <10> characterized in that the total concentration of compounds according to group c1) is in the range of 0.001% to 0.5% by weight, preferably in the range of 0.005% to 0.25% by weight, more preferably in the range of 0.01% to 0.2% by weight, still more preferably in the range of 0.025% to 0.15% by weight, calculated to the total weight of composition A.

<12> The composition according to any of the clauses <1> to <11> characterized in that one or more compound(s) according to group c2) is according to the following general structure:

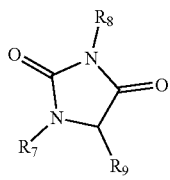

wherein $R_7$, $R_8$, and $R_9$ are independently selected from H, OH, halogen, $C_1$-$C_{12}$ linear or branched alkyl or alkenyl, O—X, COOH, phenyl, diphenyl, ureyl, and/or their salt(s), and/or their mixtures, with X being $C_1$-$C_{12}$ linear or branched alkyl.

<13> The composition according to any of the clauses <1> to <8> or <12> characterized in that one or more compound(s) according to group c2) is/are
hydantoin,
dichlordimethylhydantoin,
bromchlordimethylhydantoin,
dibromdimethylhydantoin,
ethotoin,
phenytoin,
mephenytoin,
fosphenytoin,
allantoin,
and/or their salt(s), and/or their mixtures.

<14> The composition according to any of the clauses <1> to <8> or <12> to <13> characterized in that one or more compound(s) according to group c2) is hydantoin or allantoin, and/or their salt(s), and/or their mixtures, preferably it is hydantoin and/or its salt(s).

<15> The composition according to any of the clauses <1> to <8> or <12> to <14> characterized in that the total concentration of compounds according to group c2) is in the range of 0.001% to 0.5% by weight, preferably in the range of 0.005% to 0.25% by weight, more preferably in the range of 0.01% to 0.2% by weight, still more preferably in the range of 0.025% to 0.15% by weight, calculated to the total weight of the composition A.

<16> The composition according to any of the clauses <1> to <15> characterized in that the total concentration of compounds according to group c) is in the range of 0.001% to 0.5% by weight, preferably in the range of 0.005% to 0.25% by weight, more preferably in the range of 0.01% to 0.2% by weight, still more preferably in the range of 0.025% to 0.15% by weight, calculated to the total weight of the composition A.

<17> The composition according to any of the clauses <1> to <16> characterized in that it is a solid composition, preferably a powder composition.

<18> The composition according to clause <17> characterized in that composition A comprises water at 10% by weight or less, calculated to the total weight of composition A, preferably it is an anhydrous powder composition.

<19> The composition according to any of the clauses <17> to <18> characterized in that composition A comprises one or more pulverulent excipient.

<20> The composition according to clause <19> characterized in that composition A comprises one or more organic and/or an inorganic pulverulent excipient(s).

<21> The composition according to clause <20> characterized in that organic and/or inorganic pulverulent excipients diatomaceous earth, kaolin, bentonite, starch especially corn, tapioca, rice, wheat and potato, nylon powder, montmorillonit, gypsum, sawdust and perlite.

<22> The composition according to any of the clauses <17> to <21> characterized in that the total concentration of organic and/or an inorganic pulverulent excipient is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total weight of composition A.

<23> The composition according to any of the clauses <1> to <16> characterized in that it is a liquid composition at 25° C. and atmospheric pressure and comprises less than 1% by weight of water, preferably it is anhydrous.

<24> The composition according to clause <23> characterized in that composition A comprises one or more organic solvent(s).

<25> The composition according to clause <24> characterized in that the organic solvent(s) are mono-, di-, and trivalent alcohols and/or their mixtures.

<26> The composition according to any of the clauses <23> to <25> characterized in that the organic solvent(s) is/are ethanol, n-propanol, isopropanol, propylene glycol, ethylene glycol, benzyl alcohol, phenoxyethanol, and glycerol, and/or their mixtures.

<27> The composition according to any of the clauses <23> to <26> characterized in that the total concentration of organic solvents is in the range of 75% to 98% by weight, more preferably 80% to 95% by weight, further more preferably in the range of 85% to 92% by weight, calculated to the total weight of composition A.

<28> The composition according to any of the clauses <1> to <16> characterized in that composition A is an aqueous composition having a pH in the range of 7 to 12, preferably in the range of 8 to 11.5, further more preferably in the range of 9 to 11.5.

<29> The composition according to clause <28> characterized in that it comprises water at 50% by weight or more, further more preferably at 60% by weight or more, still more preferably at 70% by weight or more, still further more preferably at 80% by weight or more, calculated to the total weight of the composition A.

<30> The composition according to any of the clauses <28> to <29> characterized in that it comprises organic solvents, preferably ethanol, benzyl alcohol, and/or phenoxyethanol, and/or their mixtures.

<31> The composition according to clause <30> characterized in that the total concentration of organic solvents is in the range of 1% to 15% by weight, preferably in the range of 2% to 10% by weight, more preferably in the range of 2% to 8% by weight, calculated to the total weight of composition A.

<32> The composition according to any of the clauses <1> to <31> characterized in that compositions A comprises one or more lipophilic compound(s) as compound(s) according to group d).

<33> The composition according to clause <32> characterized in that one or more compound(s) according to group d) is/are selected from $C_{12}$ to $C_{22}$ fatty alcohols, esters of $C_3$ to $C_{22}$ alcohols with $C_{12}$ to $C_{22}$ fatty acids, $C_8$ to $C_{22}$ fatty acids, vegetable oils, and/or silicones, and/or hydrocarbon-based products, and/or their mixtures.

<34> The composition according to any of the clauses <32> to <33> characterized in that the total concentration of compounds according to group d) is in the range of 1% to 20% by weight, preferably in the range of 2% to 15% by weight, more preferably in the range of 3% to 12% by weight, calculated to the total weight of composition A.

<35> The composition according to any of the clauses <1> to <34> characterized in that compositions A comprises one or more surfactant(s) as compound according to group e).

<36> The composition according to clause <35> characterized in that one or more compound(s) according to group e) is/are selected from non-ionic surfactants, anionic surfactants, cationic surfactants, and/or amphoteric/zwitterionic surfactants, and/or their salt(s), and/or their mixtures, preferably selected from anionic surfactants, and/or their salt(s).

<37> The composition according to any of the clauses <35> to <36> characterized in that anionic surfactants are selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures, and/or their salts.

<38> The composition according to any of the clauses <35> to <37> characterized in that non-ionic surfactants are selected from alkyl glycosides, alkyl polyglycosides, ethoxylated triglycerides, ethoxylated fatty alcohols, ethoxylated fatty acid esters, and/or their mixtures.

<39> The composition according to any of the clauses <35> to <38> characterized in that cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$, preferably selected from alkylamidoalkylamine surfactants, and/or their salts.

<40> The composition according to any of the clauses <35> to <39> characterized in that amphoteric/zwitterionic surfactants are of betaine type, preferably they are selected from alkyl betaines and/or alkylamido betaines.

<41> The composition according to any of the clauses <35> to <40> characterized in that composition A comprises one or more surfactant(s) at a total concentration in the range of 0.1% to 10% by weight, calculated to the total weight of composition A.

<42> The composition according to any of the clauses <1> to <41> characterized in that composition A comprises one or more thickening polymer(s).

<43> The composition according to clause <42> characterized in that one or more thickening polymer(s) is/are selected from non-ionic thickening polymers and/or anionic thickening polymers, and/or their salt(s), and/or their mixtures.

<44> The composition according to clause <43> characterized in that non-ionic thickening polymers is/are cellulose-based polymers, preferably methylcellulose, hydroxymethylcellulose, hydroxyethylcellulose, hydroxypropylcellulose, hydroxyethyl-methylcellulose, and alkylated hydroxyl celluloses such as ($C_2$-$C_8$)-alkylcelluloses or cetyl hydroxyethylcellulose.

<45> The composition according to any of the clauses <43> to <44> characterized in that anionic thickening polymers is/are selected from naturally-based anionic polymers and/or synthetic anionic polymers.

<46> The composition according to clause <45> characterized in that natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate, alginic acids, sodium alginates, ammonium alginates, calcium alginates, gum arabic, and guar gum.

<47> The composition according to any of the clauses <42> to <46> characterized in that synthetic anionic polymers are associative thickening polymers, such as acrylates/steareth-30 methacrylate copolymer.

<48> The composition according to any of the clauses <42> to <47> characterized in that one or more thickening polymer(s) of composition A is xanthan gum and/or dehydroxanthan gum.

<49> The composition according to any of the clauses <42> to <48> characterized in that the total concentration of thickening polymers in compositions A is in the range of 0.1% to 15% by weight, preferably in the range of 0.25% to 12% by weight, more preferably in the range of 0.5% to 10% by weight, calculated to the total weight of each of composition A.

<50> The composition according to any of the clauses <1> to <16> and <28> to <49> characterized in that composition A has a viscosity in the range of 1,000 Pas to 25,000 mPas, preferably 2,000 mPas to 20,000 mPas, more preferably in the range of 2,500 mPas to 17,500 mPas, determined by cone plate viscometry at 25° C. under atmospheric conditions.

<51> The composition according to any of the clauses <1> to <16> and <28> to <50> characterized in that composition A comprises one or more oxidizing agent(s), preferably hydrogen peroxide.

<52> The composition according to clause <51> characterized in that the concentration of hydrogen peroxide in composition A is in the range of 0.1% to 20% by weight, more preferably in the range of 0.25% to 15% by weight, further more preferably in the range of 1% to 12% by weight, calculated to the total weight of composition A.

The present disclose is also directed to <53> a kit-of-parts for dyeing keratin fibers, preferably human keratin fibers, more preferably human hair, comprising:
    a composition A as defined in any of the clauses <1> to <52>,
    a composition B having a pH in the range of 1 to 6 and optionally comprising one or more oxidizing agent(s).

<54> The kit-of-parts according to clause <53> characterized in that composition B has a pH in the range of 1.5 to 5, further more preferably in the range of 2 to 4.5

<55> The kit-of-parts according to any of the clauses <53> to <54> characterized in that composition B is an emulsion, thickened gel, or a combination thereof <56> The kit-of-parts according to any of the clauses <53> to <55> characterized in that composition B comprises one or more lipophilic compound(s) as compound(s) according to group d) as defined in any of the clauses <33> to <34> for composition A.

<57> The kit-of-parts according to any of the clauses <53> to <56> characterized in that composition B comprises one or more surfactant(s) as compound according to group e) as defined in any of the clauses <35> to <41> for composition.

<58> The kit-of-parts according to any of the clauses <53> to <57> characterized in that composition B comprises one or more thickening polymer(s) as defined in any of the clauses <42> to <49> for composition A.

<59> The kit-of-parts according to any of the clauses <53> to <58> characterized in that the concentration of hydrogen peroxide in composition B is in the range of 0.1% to 20% by weight, more preferably in the range of 0.25% to 15% by weight, further more preferably in the range of 1% to 12% by weight, calculated to the total weight of composition B.

<60> The kit-of-parts according to any of the clauses <53> to <59> characterized in that it further comprises one or more compositions selected from:
a bleaching powder composition C comprising one or more persalt(s) and/or peroxy salt(s) and one or more alkalizing agent(s),
an aqueous lightening composition D comprising one or more alkalizing agent(s) and having a pH in the range of 7 to 12.

<61> The kit-of-parts according to clause <60> characterized in that one or more persalt(s) and/or peroxy salt(s) of bleaching powder composition C is/are sodium persulfate, potassium persulfate, ammonium persulfate, earth alkali peroxides such as magnesium peroxide, melamine peroxide or urea peroxide or phthalimidoperoxy hexanoic acid.

<62> The kit-of-parts according to any of the clauses <60> to <61> characterized in that that the total concentration of persalts and/or peroxy salts in the bleaching powder composition C is in the range of 10% to 80% by weight, preferably in the range of 15% to 70% by weight, more preferably in the range of 20% to 60% by weight, and still more preferably in the range of 25% to 60% by weight, calculated to the total weight of bleaching powder composition C.

<63> The kit-of-parts according to any of the clauses <60> to <62> characterized in that that one or more alkalizing agent(s) of bleaching powder composition C is/are metasilicates and disilicates, in particular sodium metasilicate and/or sodium disilicate, preferably at a total concentration is in the range of 1% to 20% by weight, more preferably 5% to 15% by weight, calculated to the total weight of bleaching powder composition C.

<64> The kit-of-parts according to clause <60> characterized in that the aqueous lightening composition D is an emulsion comprising one or more lipophilic compound according to d), as also disclosed for composition A in any of the clauses <33> to <34>.

<65> The kit-of-parts according to any of the clauses <60> or <64> characterized in that the aqueous lightening composition D has a pH in the range of 8 to 11, more preferably in the range of 8.5 to 10.5.

<66> A kit-of-parts for dyeing keratin fibers, preferably human keratin fibers, more preferably human hair, comprising:
a first composition comprising one or more compound(s) according to group b) as defined in any of clauses <1> to <52>,
a second composition comprising one or more compound(s) according to group c) as defined in any of the clauses <1> to <52>,
wherein the first and/or second and/or an optional third composition comprise(s) one or more compound(s) according to group a) as defined in any of the clauses <1> to <52>.

<67> The kit-of-parts according to clause <66> characterized in that the first, second, and optional third compositions are kept separate until directly prior to use on keratin fibers to prepare composition A.

The present disclosure is also directed to <68> a method for dyeing of keratin fibers, preferably human keratin fibers, more preferably human hair, comprising the steps of:
i) providing a composition A as defined in any of the clauses <1> to <55>, optionally a composition B as defined in any of the clauses <53> to <59>, and/or optionally one or more further composition(s),
ii) optionally mixing the compositions A and B, or the compositions A and one further composition(s), or the compositions A, B, and one or more further composition(s), to yield a ready-to-use composition having a pH in the range of 7 to 12,
iii) applying the composition A or the ready-to-use composition of step ii) onto keratin fibers,
iv) leaving the composition A or the ready-to-use composition for a time period of 1 to 60 min and optionally heating the keratin fibers to a temperature range in the range of 40° C. to 60° C.,
v) rinsing off the keratin fibers and optionally shampooing the keratin fibers.

<69> The method according to clause <68> characterized in that the ready-to-use composition of steps ii) and iii) has a pH in the range of 7 to 12, preferably in the range of 7.5 to 11, more preferably in the range of 8.0 to 10.5.

<70> The method according to any of the clauses <68> to <69> characterized in that ready-to-use composition in step iv) is left onto keratin fibers for a time period of 1 min to 60 min, preferably for a time period of 5 min to 45 min, more preferably for a time period of 10 min to 35 min.

<71> The method according to any of the clauses <68> to <70> characterized in that during the application time of the ready-to-use mixture in step iv), heat may be applied to the keratin fibers, preferably in a temperature range from 30° C. to 50° C.

<72> The method according to any of the clauses <68> to <71> characterized in that the optional compositions of steps ii) and iii) is/are a bleaching powder composition C and/or an aqueous lightning composition D as defined in any of the clauses <67> to <67>.

The present disclosure is also directed to <73> a method of making composition A as defined in any of the clauses <1> to <52> comprising the steps of:
providing a first composition comprising one or more compound(s) according to group b) as defined in any of clauses <1> to <52>,
providing a second composition comprising one or more compound(s) according to group c) as defined in any of the clauses <1> to <52>, with the provision that the first and/or second and/or an optional third composition comprise(s) one or more compound(s) according to group a) as defined in any of the clauses <1> to <52>, mixing the first, second, and optionally third composition.

The following examples are to illustrate the invention, but not to limit it.

EXAMPLES

Example 1

The following compositions A were prepared by dissolving the compounds according to groups a), b), and c) under constant stirring in water:

|  |  | Ingredients | Inv. 1 | Comp. 1 |
|---|---|---|---|---|
|  |  |  | % by weight | |
| Composition A | a) | HC Red 18 | 0.03 | 0.03 |
|  |  | HC Blue 18 | 0.27 | 0.27 |
|  |  | HC Yellow 16 | 0.5 | 0.5 |
|  | b) | Ammonia (25% v/v) | 3.85 | 3.85 |
|  | b) | 2-amino-2-methylpropanol | 4.75 | 4.75 |
|  | c) | Caffeine | 0.025 | — |
|  | — | pH | 10.5 | |
|  | — | Water | Ad 100.0 | |

The following composition B was prepared:

|  | % by weight |
|---|---|
| Cetearyl alcohol | 4.0 |
| Sodium lauryl sulfate | 0.8 |
| Phosphoric acid | q.s. ad pH 2.5 |
| Hydrogen peroxide | 6.0 |
| Water | ad 100.0 |

The following dyeing results were obtained:

| Treatment groups | Dyeing intensity after washing, ΔE |
|---|---|
| Inv. 1 | 58.50 |
| Comp. 1 | 53.68 |

As illustrated by the results above, inventive composition 1 delivered a higher dyeing intensity after washing corresponding to a higher wash fastness in comparison to the comparative composition 1.

Example 2

The following composition A and B were prepared:

|  |  | Ingredients | Inv. 2 | Comp. 2 |
|---|---|---|---|---|
|  |  |  | % by weight | |
| Composition A | a) | Disperse Black 9 | 0.05 | 0.05 |
|  | b) | Ammonia (25% v/v) | 3.85 | 3.85 |
|  | c) | Caffeine | 0.2 | — |
|  | — | pH | 10.5 | |
|  | — | Water | Ad 100.0 | |

The same composition B of example 1 was used. The following dyeing results were obtained:

| Treatment groups | Dyeing intensity after washing, ΔE |
|---|---|
| Inv. 2 | 41.69 |
| Comp. 2 | 34.93 |

Methods

Hair Dyeing

The inventive compositions (inv.) and comparative compositions (comp.) were mixed with composition B of example 1 in a weight ratio of 1:1 to prepare a ready-to-use composition having a pH of 9.5.

To human hairstreaks (21 cm, 2 g per bundle) were applied the ready-to-use compositions as explained above and left for 30 min at room temperature. The hairstreaks were then rinsed-off with lukewarm water, shampooed with a shampoo commercially available under the trade name Goldwell Deep Cleansing Shampoo, and blow-dried. The color was measured as outlined below.

Wash fastness was determined by placing the dyed hair streaks in a water bath comprising 3.5% by weight of sodium laureth sulfate and shaking it for 30 min at 40° C. After this treatment, the hairstreak were blow-dried and the remaining color was measured (ΔE).

The colormetric data were obtained with a color-difference meter by the CIE colorimetric system (L*,a*,b*), and the color difference (ΔE) were calculated by the following formula.

$$\Delta E = \sqrt{(L_1^* - L_0^*)^2 + (a_1^* - a_0^*)^2 + (b_1^* - b_0^*)^2}$$

The invention claimed is:

1. A dyeing composition for keratin fibers, comprising:
a) one or more alkalizing agents;
b) one or more direct dyes; and
c) one or more compounds selected from the following groups:

1)

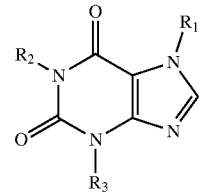

wherein $R_1$, $R_2$, and $R_3$ are independently selected from H and $CH_3$, and 2) One or more imidazolidin-2,4-diones and salts thereof, wherein the one or more direct dyes is selected from the group consisting of HC Blue 18, HC Red 18, HC Yellow 16, Disperse Black 9, Acid Yellow 1, 2-amino-6-chloro-4-nitrophenol, and salts thereof and mixtures thereof, and wherein a total concentration of the one or more alkalizing agents is in a range of 0.5% to 40% by weight, calculated to the total weight of the dyeing composition.

2. The dyeing composition according to claim 1, wherein the one or more alkalizing agents is selected from an alkanolamine, ammonia, and salts thereof.

3. The dyeing composition according to claim 1, wherein a total concentration of the one or more alkalizing agents is in a range of 0.5% to 30% by weight, calculated to the total weight of the dyeing composition.

4. The dyeing composition according to claim 1, wherein a total concentration of the one or more direct dyes is in a range of 0.001% to 10% by weight, calculated to the total weight of the dyeing composition.

5. The dyeing composition according to claim 1, wherein at least one of the one or more compounds according to group 1) is caffeine and/or theobromine.

6. The dyeing composition according to claim 1, wherein the one or more imidazolidin-2,4-diones is according to the following general structure:

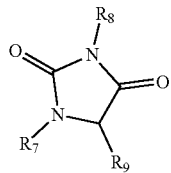

wherein $R_7$, $R_8$, and Ry are independently selected from H, OH, halogen, $C_1$-$C_{12}$ linear or branched alkyl or alkenyl, O—X, COOH, phenyl, diphenyl, ureyl, and salts thereof and X is a $C_1$-$C_{12}$ linear or branched alkyl.

7. The dyeing composition according to claim 1, wherein the one or more imidazolidin-2,4-diones is hydantoin or allantoin, and salts thereof.

8. The dyeing composition according to claim 1, wherein a total concentration of the one or more compounds according to c) is in a range of 0.001% to 0.5% by weight, calculated to the total weight of the dyeing composition.

9. The dyeing composition according to claim 1, wherein the dyeing composition is a powder composition.

10. The dyeing composition according to claim 1, wherein the dyeing composition is a liquid composition at 25° C. and atmospheric pressure and comprises less than 1% by weight of water.

11. The dyeing composition according to claim 1, wherein the dyeing composition is an aqueous composition having a pH in a range of 7 to 12.

12. A kit-of-parts for dyeing keratin fibers, comprising: the dyeing composition of claim 1; and
a composition B having a pH in a range of 1 to 6 and optionally comprising one or more oxidizing agents.

13. The kit-of-parts according to claim 12 further comprising one or more compositions selected from:

a bleaching powder composition C comprising one or more persalts and/or peroxy salts and one or more alkalizing agents, and
an aqueous lightening composition D comprising one or more alkalizing agents and having a pH in a range of 7 to 12.

14. A kit-of-parts for dyeing keratin fibers, comprising:
a first composition comprising the one or more direct dyes of claim 1; and
a second composition comprising the one or more compounds of claim 1,
wherein the first and/or second and/or an optional third composition comprises the one or more alkalizing agents of claim 1.

15. A method for dyeing of keratin fibers, comprising:
optionally mixing the dyeing composition of claim 1 and a composition B having a pH in a range of 1 to 6 and optionally comprising one or more oxidizing agents, or the dyeing composition and one or more further compositions, or the dyeing composition, the composition B, and one or more further compositions, to yield a ready-to-use composition having a pH in a range of 7 to 12;
applying the dyeing composition or the ready-to-use composition onto the keratin fibers;
leaving the dyeing composition or the ready-to-use composition for a time period of 1 to 60 min and optionally heating the keratin fibers to a temperature range in a range of 40° C. to 60° C.; and
rinsing off the keratin fibers and optionally shampooing the keratin fibers.

16. The dyeing composition according to claim 1, wherein the one or more alkalizing agents are selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethane, and salts thereof.

17. The dyeing composition according to claim 1, wherein a total concentration of the one or more alkalizing agents is in a range of 1% to 25% by weight, calculated to the total weight of the dyeing composition.

18. The dyeing composition according to claim 1, wherein a total concentration of the one or more direct dyes is in a range of 0.01% to 1.5% by weight, calculated to the total weight of the dyeing composition.

19. The dyeing composition according to claim 1, wherein a total concentration of the one or more compounds according to c) is in a range of 0.025% to 0.15% by weight, calculated to the total weight of the dyeing composition.

* * * * *